United States Patent [19]

Ray et al.

[11] Patent Number: 4,557,258
[45] Date of Patent: Dec. 10, 1985

[54] PROXIMAL TIBIAL CUFF

[75] Inventors: James M. Ray; Thomas M. McConnell, both of Orlando, Fla.

[73] Assignee: Ray-McConnell, Inc., Orlando, Fla.

[21] Appl. No.: 543,903

[22] Filed: Oct. 20, 1983

[51] Int. Cl.⁴ ............................................. A61F 13/04
[52] U.S. Cl. ................................................. 128/87 R
[58] Field of Search ............... 128/82, 83, 87, 89 R, 128/90, 91 R; 3/16, 17, 19

[56] References Cited

U.S. PATENT DOCUMENTS

| D. 265,248 | 6/1982 | Grigorieff . | |
|---|---|---|---|
| 3,032,033 | 5/1962 | Ramirez | 128/90 |
| 3,070,091 | 12/1962 | Barnard | 128/89 |
| 3,643,656 | 2/1972 | Young et al. | 128/90 |
| 3,680,549 | 8/1972 | Lehneis et al. | 128/80 |
| 3,909,855 | 10/1975 | Barredo | 3/16 |
| 4,268,922 | 5/1981 | Marsh et al. | 128/89 R |
| 4,274,166 | 6/1981 | Chambers | 3/17 |
| 4,409,972 | 10/1983 | Prahl | 3/19 |

FOREIGN PATENT DOCUMENTS 2054922  5/1971  France .

Primary Examiner—C. Fred Rosenbaum
Assistant Examiner—Christa K. Scott
Attorney, Agent, or Firm—Shapiro and Shapiro

[57] ABSTRACT

A proximal tibial cuff which may be integrated with a cast for a lower leg fracture is stabilized on the leg by inner surfaces which conform to the injured limb and by an anterior inward projection which impresses soft tissue distal to the patella, anterior to the patellar tendon.

10 Claims, 8 Drawing Figures

PROXIMAL TIBIAL CUFF

BACKGROUND OF THE INVENTION

The present invention concerns a proximal tibial cuff for use in the treatment of fractures of the lower leg.

As is well known, the treatment of a lower leg fracture typically involves the application of a plaster cast or the like to a patient's injured limb. In order to achieve proper healing of the fracture with a minimum of inconvenience to the patient, a cast should be both stable and comfortable and should not interfere significantly with movement of the knee. In addition, to further the healing process, it is also desirable that a lower leg cast minimize the exposure of the fracture area to weight-bearing forces when the patient stands on the injured leg. The present invention is directed toward the foregoing considerations.

SUMMARY OF THE INVENTION

Accordingly, the present invention provides a proximal tibial cuff which, in a principal aspect, may comprise a sleeve including a lower portion of interior cross section substantially conforming to the leg and an upper portion of interior cross section substantially conforming to the knee, the upper portion having an anterior inward projection for impressing the soft tissues distal to the patella, anterior to the patellar tendon.

In a preferred form, the cuff also includes rotation-preventing means, such as a pair of wings which conform to the sides of the knee; a longitudinal split to facilitate application to the leg; an outwardly curved upper posterior edge to avoid irritating contact with the skin and interference with movement of the knee; and means, for example defining a plurality of holes, to improve bonding between the cuff and a lower leg cast.

As will be understood from the detailed description below, a proximal tibial cuff according to the invention may be integrated with a lower leg cast to provide a stable and comfortable cast structure which permits substantially full use of the knee and which promotes the healing process by transmitting weight-bearing forces around the fracture area to the upper leg. Further advantages of the invention will also be apparent from the ensuing discussion in which reference is made to the following drawings.

DETAILED DESCRIPTION OF THE INVENTION

Figure 1:
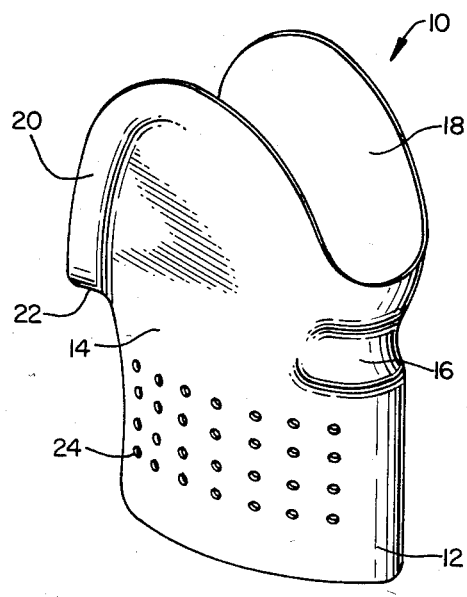
FIG. 1 is a perspective view of a proximal tibial cuff for the right leg in accordance with the invention.

Referring to the details of the invention as illustrated in the drawings, a proximal tibial cuff in the preferred form for the right leg will now be described. It will be appreciated that while the illustrated embodiment is specifically adapted for use on the right leg, a similar cuff for the left leg may be obtained simply by mirroring the features of the cuff shown.

Figure 3:
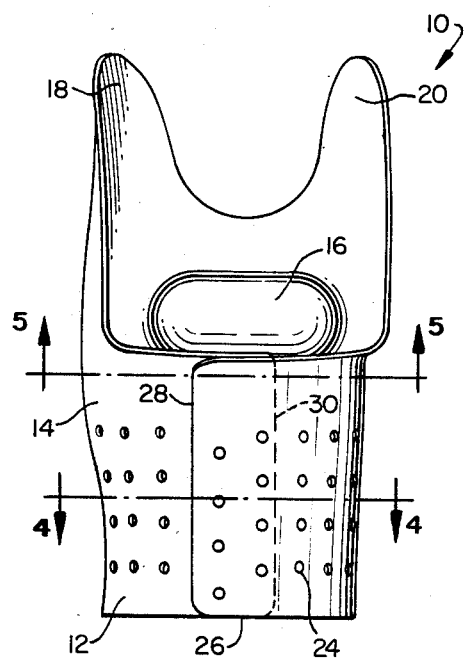
FIG. 3 is a rear elevation of the cuff shown in FIG. 1.
Figure 4:
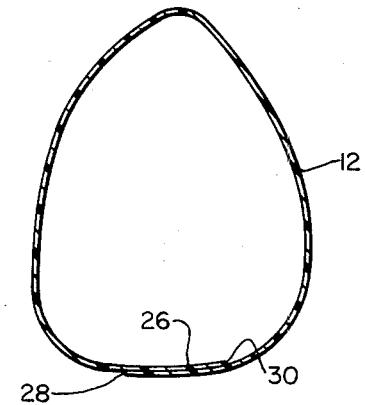
FIG. 4 is a cross-sectional view along line 4—4 in FIG. 3.
Figure 5:
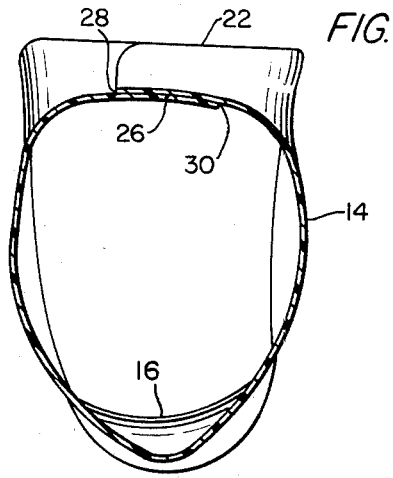
FIG. 5 is a cross-sectional view along line 5—5 in FIG. 3.

As shown in FIGS. 1–5, a proximal tibial cuff according to the invention may comprise a sleeve 10, including a lower portion 12 of interior cross-section substantially conforming to the leg (see FIG. 4) and an upper portion 14 of interior cross-section substantially conforming to the knee (see FIG. 5). The sleeve is preferably made of a material which provides sufficient axial rigidity to support weight-bearing forces along the length of the sleeve without appreciable deformation. Although, as will be apparent to those skilled in the art, a variety of materials are suitable for this purpose, a resilient plastic such as polyethylene is preferred so that the sleeve will be somewhat flexible transversely to its axis. A proximal tibial cuff with such flexibility will be both easy to apply (as will be discussed below) and capable of accommodating a range of leg sizes, thereby permitting the use of several standard cuff sizes.

According to an important aspect of the invention, the upper portion 14 of the sleeve is provided with an anterior inward projection 16. The projection 16 is adapted to impress the soft tissue (i.e., the skin and subcutaneous tissue) distal to the patella, anterior to the patellar tendon. As will be discussed later, this action of projection 16 serves to stabilize the cuff when it is applied to the leg. It should be noted that projection 16 impresses the soft tissues only to a degree sufficient to stabilize the proximal tibial cuff and does not unduly constrict the knee.

Figure 2:
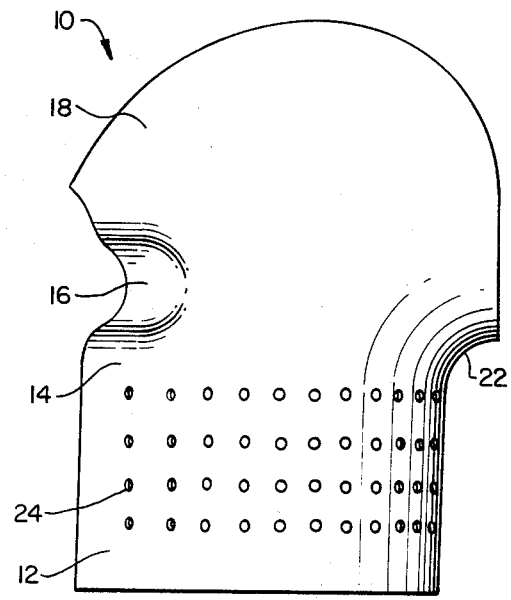
FIG. 2 is a left elevation of the cuff shown in FIG. 1.

To ensure further the rotational stability of the cuff, the sleeve is provided with rotation-preventing wing members 18 and 20 which extend from the upper portion 14 thereof (see FIGS. 1 and 3). As shown, wings 18 and 20 are preferably designed substantially to conform to the medial and lateral regions of the knee, respectively, and the upper edges thereof are flared outwardly to avoid irritating contact with the skin. Similarly, as shown in FIG. 2, it is preferable that the upper posterior edge 22 of the sleeve be curved outwardly to ensure patient comfort. The outward curvature of edge 22 provides a smooth surface for contacting the skin and permits substantially full flection of the knee without interference from the cuff.

As is best seen in FIGS. 3–5, the present embodiment of the proximal tibial cuff also includes a longitudinal split 26 to facilitate its application to the leg. In the form shown, longitudinal split 26 runs through the posterior of the cuff, approximately at the center. When the cuff is made of a resilient plastic (e.g., polyethylene) as discussed above, the edges 28 and 30 of the split may overlap as shown to accommodate variations in leg size, and the cuff may be applied simply by spreading edges 28 and 30 and placing it around the leg. The cuff will then return to the proper shape due to the resilience of the plastic.

Figure 6:
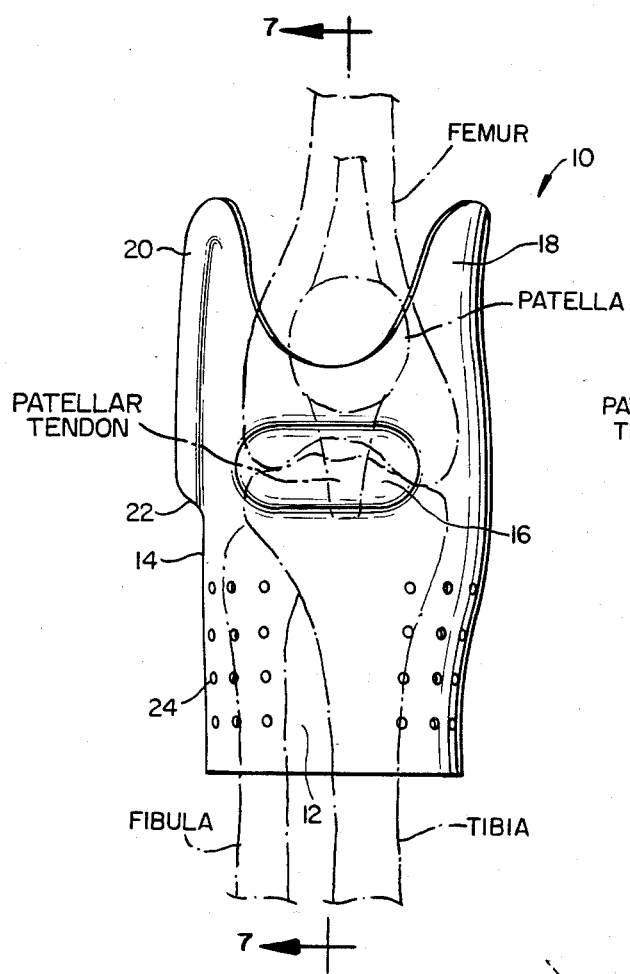
FIG. 6 is a front view of the proximal tibial cuff of FIG. 1 showing the position of the cuff in use relative to the bones of the right leg.
Figure 7:
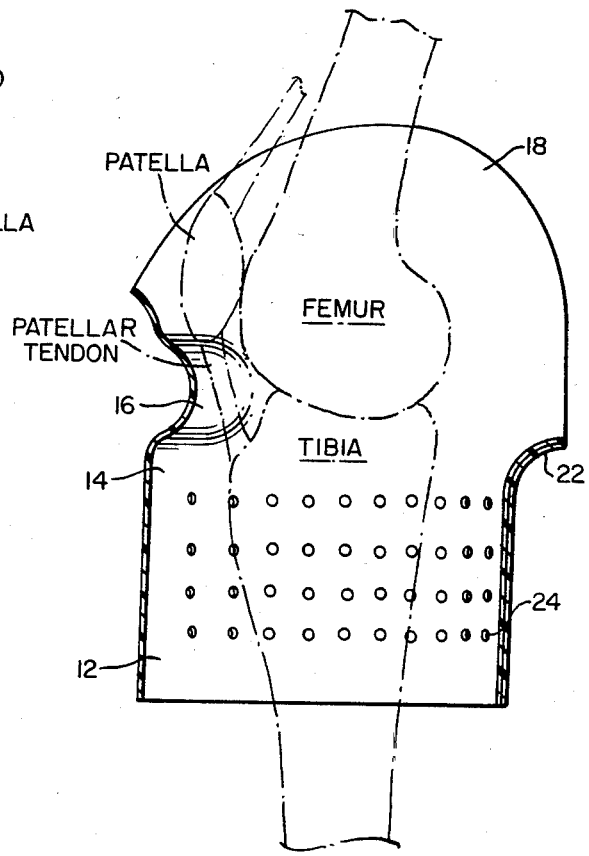
FIG. 7 is a cross-sectional view along line 7—7 in FIG. 6.

The preferred position of the proximal tibial cuff when applied to the right leg is depicted in FIGS. 6 and 7. As shown, the projection 16 is located distal to the patella, anterior to the patellar tendon, with the lower and upper portions of the sleeve 12 and 14 conforming to the knee and leg and wings 18 and 20 conforming to the medial and lateral regions of the knee as previously described.

With the cuff in position as shown, its conforming inner surfaces act to maintain it in a substantially stable position. More importantly, however, anterior inward projection 16, by impressing the soft tissues as described above, provides an additional degree of stability which effectively fixes the position of the cuff on the leg.

Figure 8:
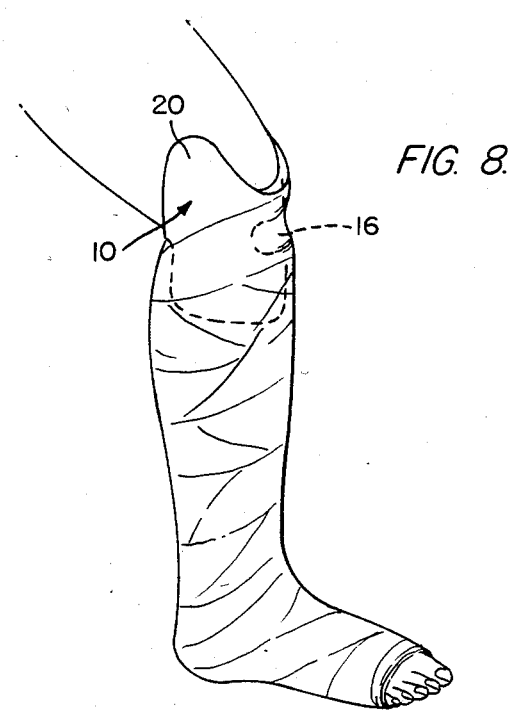
FIG. 8 is a perspective view of a proximal tibial cuff according to the invention integrated with a cast on the lower right leg of a patient.

After the cuff has been applied to the leg, a plaster cast or the like can be molded over the cuff as shown in FIG. 8. Generally, in the case of a lower leg fracture, the cast will encompass substantially the entire lower leg, including a portion of the foot (see FIG. 8). When the cast hardens, it will bond firmly to the cuff to form a rigid, integrated cast structure. To improve bonding between the cuff and the cast material means defining a plurality of holes 24 (or other bonding improvement means such as surface projections) may be incorporated in the cuff as shown in FIGS. 1-3.

It is readily apparent that the integrated cast structure just described will be both stable and comfortable about the proximal tibial region. In particular, because the cuff is stabilized in position as previously discussed and the hardened cast material is bonded firmly to the cuff, the entire cast structure will necessarily be stable about the proximal tibial region. Furthermore, because it is primarily the cuff which is in direct contact with the leg in this region, this stability is achieved without sacrifice of patient comfort or interference with use of the knee.

Beyond the foregoing advantages, the integrated cast structure (incorporating the proximal tibial cuff as described) forms a rigid weight-bearing member which promotes the healing process by transmitting weight-bearing forces from the upper leg to the foot, bypassing the fracture area.

While the foregoing discussion describes a preferred embodiment of the invention, it will be apparent to those skilled in the art that changes can be made without departing from the principles and spirit of the invention, the scope of which is defined in the appended claims.

The invention claimed is:

1. A proximal tibial cuff, comprising a sleeve including:
   a lower portion of interior cross-section substantially conforming to the leg and
   an upper portion of interior cross-section substantially conforming to the knee, said upper portion having anterior inward projection means for impressing soft tissue distal to the patella, anterior to the patellar tendon.

2. A proximal tibial cuff as recited in claim 1, wherein said sleeve includes means for preventing rotation thereof.

3. A proximal tibial cuff as recited in claim 2, wherein said rotation-preventing means comprises a pair of wings extending from said upper sleeve portion and substantially conforming to the sides of the knee.

4. A proximal tibial cuff as recited in claim 1, wherein said sleeve includes means defining a longitudinal split to facilitate application of the sleeve to the leg.

5. A proximal tibial cuff as recited in claim 4, wherein the edges of said longitudinal split overlap.

6. A proximal tibial cuff as recited in claim 1, wherein the upper posterior edge of said sleeve is curved outwardly.

7. A proximal tibial cuff as recited in claim 1, wherein said sleeve is open throughout its length and configured to receive the knee through one end and to receive the lower leg through another end and wherein said sleeve includes means for improving bonding between the sleeve and a cast for the lower leg.

8. A proximal tibial cuff as recited in claim 7, wherein said bonding improving means defines a plurality of holes.

9. A proximal tibial cuff, comprising a sleeve including:
   a lower portion of interior cross-section substantially conforming to the leg,
   an upper portion of interior cross-section substantially conforming to the knee,
   an outwardly curved upper posterior edge,
   means defining a longitudinal split in the sleeve to facilitate application of said sleeve to the leg, and
   means defining a plurality of holes in the sleeve to improve bonding between said sleeve and a cast for the lower leg; and
   wherein said upper sleeve portion has a pair of wings extending therefrom and substantially conforming to the sides of the knee and anterior inward projection means for impressing soft tissue distal to the patella, anterior to the patellar tendon.

10. In combination with a cast for the lower leg, a proximal tibial cuff, comprising a sleeve including:
    a lower portion of interior cross-section substantially conforming to the leg and
    an upper portion of interior cross-section substantially conforming to the knee, said upper portion having an anterior inward projection for impressing soft tissue distal to the patella, anterior to the patellar tendon,
    said sleeve having means for bonding the same to said cast.

* * * * *